(12) United States Patent
Carson et al.

(10) Patent No.: US 6,492,387 B2
(45) Date of Patent: Dec. 10, 2002

(54) ISOINDOLYL AND ISOQUINOLINYL AROYL PYRROLE COMPOUNDS

(75) Inventors: John R. Carson, Norristown, PA (US); Philip M. Pitis, North Wales, PA (US)

(73) Assignee: Ortho-McNeil Pharamaceutical, Inc., Raritan, NJ (US)

( * ) Notice: Subject to any disclaimer, the term of this patent is extended or adjusted under 35 U.S.C. 154(b) by 0 days.

(21) Appl. No.: 10/015,038

(22) Filed: Dec. 11, 2001

(65) Prior Publication Data

US 2002/0128286 A1 Sep. 12, 2002

Related U.S. Application Data

(60) Provisional application No. 60/256,865, filed on Dec. 20, 2000.

(51) Int. Cl.$^7$ .................. C07D 40/102; A61K 31/47; A61K 31/40
(52) U.S. Cl. ................ 514/307; 514/416; 546/146; 548/465
(58) Field of Search ................ 514/307, 416; 546/146; 548/465

(56) References Cited

U.S. PATENT DOCUMENTS

| | | |
|---|---|---|
| 5,332,736 A | 7/1994 | Carmosin et al. |
| 5,760,007 A | 6/1998 | Shank et al. |
| 6,191,142 B1 | 2/2001 | Carson et al. |
| 2002/0019436 A1 | 2/2002 | Carson |

OTHER PUBLICATIONS

A Pilot Study, Fr. Eur. Neurol. 1998, 40(4), 191–200 Nadin, Attal et al.
Drugs of the Future, 1991, (16) 317–320.
Swinyard et al., J. Pharmacol Exptl. Therap, 106, 319 (1952).
S.H. Chung & J.M. Chung, An Experimental Model for Peripheral Neuropathy Produced by Segmental Spinal Nerve Ligation in the Rat, Pain, 1992, 50, 355–363.
Chaplan, Pogrel, Yaksh, Pharmacol Exp. Ther. 1994, 269, 1117–1123.
L.S. Goodman et al., "The Pharmacological Basis of Therapeutics" 5th Ed., pp. 201–226, Macmillan (1975).
J. White & G. McGillvrey, J. Org. Chem, 1977, 42, 4248–4251.
R.L. Krall, J.K. Penry, B.G. White, H.J. Kupferberg, and E.A. Swinyard, Epilepsia, 19:409–428, 1978.
J.R. Carson et al., "Aroy(aminoacyl)pyrroles, a New Class of Anticonvulsant Agents", J. Med. Chem. 1997, 40, pp. 1578–1584, American Chemical Society 1997.
Communication Relating to the Partial Results of PCT International Search Report, dated Jun. 11, 2002 for PCT Appln. No. PCT/US01/47639 which relates to U.S. Appln. No. 10/015,038.

*Primary Examiner*—Zinna Northington Davis
(74) *Attorney, Agent, or Firm*—John W. Harbour

(57) ABSTRACT

This invention is directed to isoindolyl and isoquinolinyl aroyl pyrrole compounds pharmaceutically useful as agents or modulators for the treatment of central nervous system disorders and methods for the treatment of central nervous system disorders.

23 Claims, No Drawings

ISOINDOLYL AND ISOQUINOLINYL AROYL PYRROLE COMPOUNDS

This application claims the benefit of U.S. Serial No. 60/256,865, a provisional application, filed on Dec. 20, 2000, which is hereby incorporated by reference in its entirety.

FIELD OF THE INVENTION

This invention relates to compounds useful as agents for the treatment of central nervous system disorders. More particularly, this invention relates to isoindolyl and isoquinolinyl aroyl pyrrole compounds useful as agents or modulators for the treatment of central nervous system disorders including, but not limited to, epilepsy and neuropathic pain and methods for the treatment thereof.

BACKGROUND OF THE INVENTION

The conditions grouped under the term "central nervous system disorder" constitute an area of continuing medical need. Such conditions include those disorders associated with convulsions, epilepsy, neuroprotective diseases, muscle tension and neuropathic pain.

Epilepsy continues to be an area of development for new drugs and therapies. The structures of newer anticonvulsants has been summarized in Drugs of the Future, 1991, (16) 317–320.However, the impact of such drugs and therapies have yet to be fully evaluated.

Neuropathic pain is defined as pain caused by aberrant somatosensory processing in the peripheral or central nervous system. Chronic or debilitating conditions, such as post-herpetic neuralgia and phantom limb syndrome, are categorized as neuropathic pain.

Central nervous system disorders are widespread and cause pain and suffering. Moreover, current methods of treating such disorders are often inadequate.

Anticonvulsants have been suggested for the treatment of neuropathic pain. Nadin Attal, et al., Effects of Gabapentin on the Different Components of Peripheral and Central Neuropathic Pain Syndromes: A Pilot Study, *Fr. Eur. Neurol.* 1998, 40(4), 191–200 describes the anticonvulsant gabapentin having the following formula:

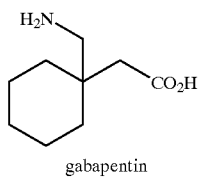

gabapentin

U.S. Pat. No. 5,760,007 describes other anticonvulsants useful in the treatment of neuropathic pain. More particularly, the reference describes the use of the anticonvulsant topiramate in treating neuropathic pain, wherein topiramate has the following general formula:

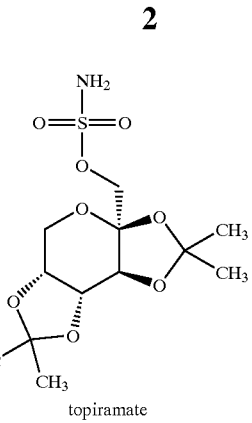

topiramate

U.S. Pat. No. 5,332,736 (hereby incorporated by reference) describes substituted aroyl aminoacyl pyrrole compounds of the formula:

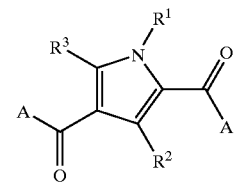

wherein,

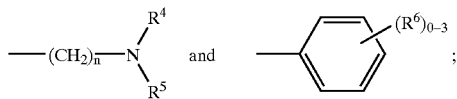

A is simultaneously both
n is selected from 1 to 5;
$R^1$ is selected from the group consisting of H and $C_{1-4}$alkyl;
$R^2$ and $R^3$ are selected from the group consisting of H and $C_{1-4}$alkyl;
$R^4$ and $R^5$ are independently selected from the group consisting of H, and $C_{1-4}$alkyl, phenyl $C_{1-4}$alkyl and substituted phenyl $C_{1-4}$alkyl where the substituent is on phenyl and selected from the group consisting of methyl and methoxy, or in the alternative, are fused and together with said nitrogen form a heterocyclic ring selected from the group consisting of:

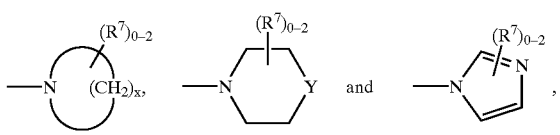

wherein Y is S or O, x is 3 to 7 and $R^7$ is selected from the group consisting of methyl and hydroxymethyl; and $R^6$ is selected from the group consisting of halo, $C_{1-4}$alkyl, $C_{1-4}$alkoxy, hydroxy, nitro, amino, $C_{1-4}$acylamino, cyano, trihalo$C_{1-4}$alkyl, $C_{1-4}$alkylsulfonyl, $C_{1-4}$alkylsulfinyl and $C_{1-4}$acyl, including pharmaceutically acceptable acid addition salts thereof as useful anticonvulsants.

U.S. patent application Ser. No. 09/505,916, filed on Feb. 17, 2000 (hereby incorporated by reference) describes aroyl aminoacyl pyrrole compounds of the formula:

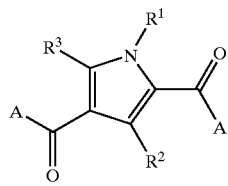

wherein,

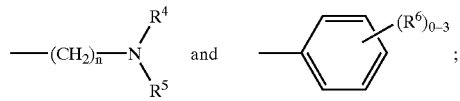

A is simultaneously both n is an integer from 1 to 5;

$R^1$ is selected from the group consisting of H and $C_{1-4}$alkyl;

$R^2$ and $R^3$ are selected from the group consisting of H and $C_{1-4}$alkyl; $R^4$ and $R^5$ are independently selected from the group consisting of H, $C_{1-4}$alkyl, phenyl $C_{1-4}$alkyl and substituted phenyl $C_{1-4}$alkyl where the substituent is on phenyl and selected from the group consisting of methyl and methoxy, or in the alternative, are fused and together with said nitrogen form a heterocyclic ring selected from the group consisting of 4-[bis(4-fluorophenyl)methylene]-piperidin-1-yl, 1,2,3,4-tetrahydro-6,7-dimethoxy-isoquinolin-2-yl,

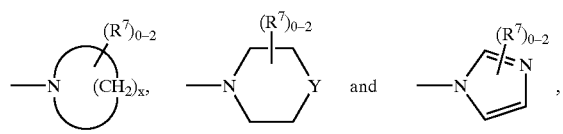

wherein Y is S or O, x is 3 to 7 and $R^7$ is selected from the group consisting of methyl and hydroxymethyl; and $R^6$ is selected from the group consisting of halo, $C_{1-4}$alkyl, $C_{1-4}$alkoxy, hydroxy, nitro, amino, $C_{1-4}$acylamino, cyano, trihalo$C_{1-4}$alkyl, $C_{1-4}$alkylsulfonyl, $C_{1-4}$alkylsulfinyl and $C_{1-4}$acyl, including pharmaceutically acceptable acid addition salts thereof as useful in the treatment of neuropathic pain.

U.S. patent application Ser. No. 60/215272, filed on Jun. 30, 2000 (hereby incorporated by reference) describes aroyl aminoacyl pyrrole compounds of Formula (I) and Formula (II):

Formula (I)

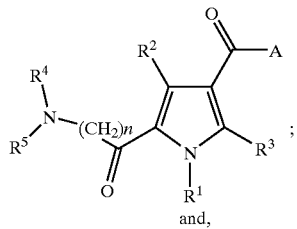

and,

Formula (II)

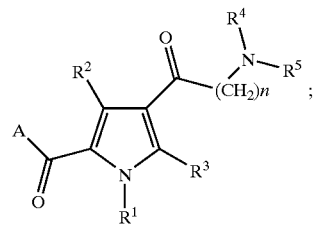

wherein

A is a substituent selected from the group consisting of aryl and heteroaryl optionally substituted with one to two substituents selected from the group consisting of halogen, $C_{1-8}$alkyl, $C_{1-8}$alkyl, alkoxy, tri(halogen) $C_{1-8}$alkyl and tri(halogen)$C_{1-8}$alkoxy; n is an integer from 1 to 5; $R^1$ is $C_{1-8}$alkyl optionally substituted with one to two substituents independently selected from the group consisting of hydroxy, $C_{1-8}$alkoxy (optionally substituted with —S$C_{1-8}$alkyl), $C_{1-8}$acyl, carboxy, carbonyl (further substituted with $C_{1-8}$alkyl, $C_{1-8}$alkoxy, amino or —S$C_{1-8}$alkyl), oxy (further substituted with carbonyl$C_{1-8}$alkyl, carbonyl$C_{1-8}$alkoxy or carbonylamino), amino (optionally further substituted with one or two substituents independently selected from $C_{1-8}$alkyl, $C_{1-8}$acyl, carbonyl$C_{1-8}$alkyl, carbonyl$C_{1-8}$alkoxy, sulfinyl$C_{1-8}$alkyl or sulfonyl $C_{1-8}$alkyl), ureido (optionally further substituted with $C_{1-8}$alkyl), thio (optionally further substituted with $C_{1-8}$alkyl or amino), sulfinyl (optionally further substituted with $C_{1-8}$alkyl or amino) and sulfonyl (optionally further substituted with $C_{1-8}$alkyl or amino); $R^2$ and $R^3$ are substituents independently selected from the group consisting of hydrogen and $C_{1-8}$alkyl; $R^4$ and $R^5$ are substituents independently selected from the group consisting of hydrogen, $C_{1-8}$alkyl and aryl$C_{1-8}$alkyl; wherein aryl is optionally substituted with one to three substituents selected from the group consisting of $C_{1-8}$alkyl, $C_{1-8}$alkoxy, tri(halo)$C_{1-8}$alkyl and tri(halo) $C_{1-8}$alkoxy; or, in the alternative, $R^4$ and $R^5$ may be fused together with nitrogen to form a heterocyclic ring selected from the group consisting of:

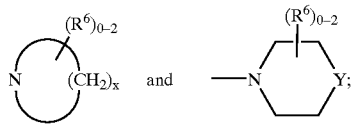

—(heteroaryl)—$(R^6)_{0-2}$, wherein x is an integer from 3 to 7 and Y is selected from the group consisting of N, S, S=O, $SO_2$ and O; and $R^6$ is a substituent selected from the group consisting of $C_{1-8}$alkyl and hydroxy$C_{1-8}$alkyl; and pharmaceutically acceptable acid addition salts thereof; with the proviso that, in the case of compound wherein n is an integer from 1 to 5; $R^1$ is selected from the group consisting of hydrogen and $C_{1-4}$alkyl; $R^2$ and $R^3$ are selected from the group consisting of hydrogen and $C_{1-4}$alkyl; $R^4$ and $R^5$ are independently selected from the group consisting of hydrogen, $C_{1-4}$alkyl, phenyl$C_{1-4}$alkyl and substituted phenyl$C_{1-4}$alkyl where the substituent is on phenyl and selected from the group consisting of methyl and methoxy; or in the alternative, are fused and together with the nitrogen form a heterocyclic ring selected from the group consisting of: 4-[bis(4-fluorophenyl) methylene]-piperidin-1-yl, 1,2,3,4-tetrahydro-6,7-dimethoxy-isoquinolin-2-yl,

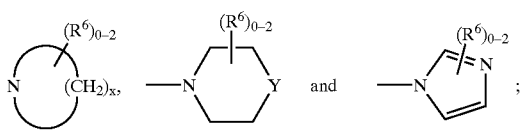

and wherein Y is S or O and x is 3 to 7; and, $R^6$ is selected from the group consisting of methyl and hydroxymethyl; then, A cannot be substituted or unsubstituted phenyl as agents for the treatment of central nervous system disorders.

The isoindolyl and isoquinolinyl aroyl pyrrole compounds of the present invention have not been previously described as useful agents for the treatment of central nervous system disorders.

Accordingly, it is an object of the present invention to provide isoindolyl and isoquinolinyl aroyl pyrrole compounds useful as agents for the treatment of central nervous system disorders. It is also an object of the present invention to teach a method for the treatment of central nervous system disorders using the isoindolyl and isoquinolinyl aroyl pyrrole compounds of the present invention.

SUMMARY OF THE INVENTION

The present invention provides substituted isoindolyl and isoquinolinyl pyrrole compounds as agents for the treatment of central nervous system disorders of Formula (I) and Formula (II):

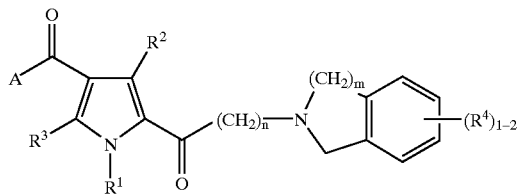

Formula (I)

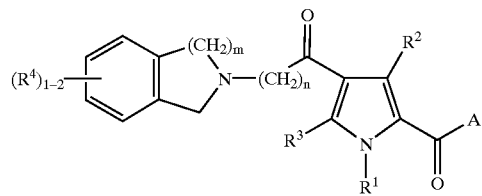

Formula (II)

wherein
A is selected from the group consisting of aryl and heteroaryl optionally substituted with one to two substituents independently selected from the group consisting of $C_{1-4}$alkyl, $C_{1-4}$alkoxy, aryl, aryl($C_{1-4}$)alkyl, amino (optionally substituted with one or two substituents independently selected from $C_{1-4}$alkyl), amino($C_{1-4}$)alkyl (wherein amino is optionally substituted with one or two substituents independently selected from $C_{1-4}$alkyl), $C_{1-4}$alkylthio, $C_{1-4}$alkylsulfinyl, $C_{1-4}$alkylsulfonyl, halogen, tri(halo) $C_{1-4}$alkyl, tri(halo)$C_{1-4}$alkoxy, hydroxy, hydroxy$C_{1-4}$alkyl, cyano and nitro;

$R^1$, $R^2$ and $R^3$ are independently selected from the group consisting of hydrogen and $C_{1-4}$alkyl;
$R^4$ is independently selected from the group consisting of hydrogen, $C_{1-4}$alkyl, $C_{1-4}$alkoxy, aryl, aryl($C_{1-4}$)alkyl, amino (optionally substituted with one or two substituents independently selected from $C_{1-4}$alkyl), amino($C_{1-4}$)alkyl (wherein amino is optionally substituted with one or two substituents independently selected from $C_{1-4}$alkyl), halogen, tri(halo)$C_{1-4}$alkyl, tri(halo)$C_{1-4}$alkoxy, hydroxy, hydroxy$C_{1-4}$alkyl, cyano and nitro;
n is an integer from 1 to 5; and,
m is an integer from 1 to 2;
and pharmaceutically acceptable acid addition salts thereof; with the proviso that a compound selected from Formula (I) cannot be 2-(3,4-dihydro-6,7-dimethoxy-2(1H)-isoquinolinyl)-1-[5-(4-methoxybenzoyl)-1-methyl-1H-pyrrol-3-yl]-ethanone.

DETAILED DESCRIPTION OF THE INVENTION

An embodiment of the present invention includes those compounds wherein, preferably, A is phenyl optionally substituted with one to two substituents independently selected from the group consisting of $C_{1-4}$alkyl, $C_{1-4}$alkoxy, phenyl, phenyl($C_{1-4}$)alkyl, amino (optionally substituted with one or two substituents independently selected from $C_{1-4}$alkyl), amino($C_{1-4}$)alkyl (wherein amino is optionally substituted with one or two substituents independently selected from $C_{1-4}$alkyl), $C_{1-4}$alkylthio, $C_{1-4}$alkylsulfinyl, $C_{1-4}$alkylsulfonyl, halogen, trifluoro$C_{1-4}$alkyl, trifluoro $C_{1-4}$alkoxy, hydroxy, hydroxy$C_{1-4}$alkyl, cyano and nitro.

More preferably, A is phenyl optionally substituted with one to two substituents independently selected from the group consisting of methyl, ethyl, n-propyl, n-butyl, i-butyl, t-butyl, methoxy, ethoxy, propoxy, phenyl, benzyl, phenethyl, phenylpropyl, amino, N-($C_{1-3}$alkyl)amino, N,N-di($C_{1-3}$alkyl)amino, amino($C_{1-3}$)alkyl, N-($C_{1-3}$alkyl)amino ($C_{1-3}$)alkyl, N,N-di($C_{1-3}$alkyl)amino($C_{1-3}$)alkyl, methylthio, ethylthio, n-propylthio, n-butylthio, i-butylthio, methylsulfinyl, ethylsulfinyl, n-propylsulfinyl, n-butylsulfinyl, i-butylsulfinyl, methylsulfonyl, ethylsulfonyl, n-propylsulfonyl, n-butylsulfonyl, i-butylsulfonyl, chlorine, fluorine, trifluoromethyl, trifluoromethoxy, hydroxy, hydroxymethyl, hydroxyethyl and hydroxypropyl.

Most preferably, A is phenyl optionally substituted with one to two substituents independently selected from the group consisting of methoxy, methylthio, methylsulfinyl, methylsulfonyl, chlorine and fluorine.

An embodiment of the present invention also includes those compounds wherein, preferably, $R^1$, $R^2$ and $R^3$ are independently selected from the group consisting of hydrogen, methyl, ethyl and propyl. More preferably, $R^1$, $R^2$ and $R^3$ are independently selected from the group consisting of hydrogen and methyl.

An embodiment of the present invention further includes those compounds wherein, preferably, $R^4$ is independently selected from the group consisting of hydrogen, $C_{1-4}$alkyl, $C_4$alkoxy, phenyl, phenyl($C_{1-4}$)alkyl, amino (optionally substituted with one or two substituents independently selected from $C_{1-4}$alkyl), amino($C_{1-4}$)alkyl (wherein amino is optionally substituted with one or two substituents independently selected from $C_{1-4}$alkyl), halogen, trifluoro$C_{1-4}$alkyl, trifluoro$C_{1-4}$alkoxy, hydroxy, hydroxy$C_{1-4}$alkyl, cyano and nitro.

More preferably, $R^4$ is independently selected from the group consisting of hydrogen, methyl, ethyl, n-propyl, n-butyl, i-butyl, t-butyl, methoxy, ethoxy, propoxy, phenyl, benzyl, phenethyl, phenylpropyl, amino, N-($C_{1-3}$alkyl)amino, N,N-di($C_{1-3}$alkyl)amino, amino($C_{1-3}$)alkyl, N-($C_{1-3}$alkyl)amino($C_{1-3}$)alkyl, N,N-di($C_{1-3}$alkyl)amino($C_{1-3}$)alkyl, chlorine, fluorine, trifluoromethyl, fluoromethoxy, hydroxy, hydroxymethyl, hydroxyethyl and hydroxypropyl.

Most preferably, $R^4$ is independently selected from the group consisting hydrogen and methoxy.

Embodiments of the present invention include those compounds wherein an integer from 1 to 2.

Exemplifying the invention is a compound selected from Table 1:

TABLE 1

| Cpd | Compound Name |
|---|---|
| 1 | 2-(3,4-dihydro-6,7-dimethoxy-2(1H)-isoquinolinyl)-1-[5-(4-fluorobenzoyl)-1-methyl-1 H-pyrrol-3-yl]-ethanone; |
| 2 | 2-(3,4-dihydro-2(1H)-isoquinolinyl)-1-[5-(4-fluorobenzoyl)-1-methyl-1H-pyrrol-3-yl]-ethanone; |
| 3 | 1-[5-(4-chlorobenzoyl)-1,2,4-trimethyl-1H-pyrrol-3-yl]-2-(3,4-dihydro-6,7-dimethoxy-2(1H)-isoquinolinyl)-ethanone; |
| 4 | 2-(3,4-dihydro-6,7-dimethoxy-2(1H)-isoquinolinyl)-1-[1-methyl-5-[4-(methylthio)benzoyl]-1H-pyrrol-3-yl]-ethanone; |
| 5 | 1-(5-benzoyl-1-methyl-1H-pyrrol-3-yl)-2-(3,4-dihydro-6,7-dimethoxy-2(1H)-isoquinolinyl)-ethanone; |
| 6 | 1-(5-benzoyl-1-methyl-1H-pyrrol-3-yl)-2-(3,4-dihydro-2(1H)-isoquinolinyl)-ethanone; |
| 7 | 2-(3,4-dihydro-6,7-dimethoxy-2(1H)-isoquinolinyl)-1-[1-methyl-5-[4-(methylsulfonyl)benzoyl]-1H-pyrrol-3-yl]-ethanone; or, |
| 8 | 2-(3,4-dihydro-6,7-dimethoxy-2(1H)-isoquinolinyl)-1-[1-methyl-5-[4-(methylsulfinyl)benzoyl]-1H-pyrrol-3-yl]-ethanone; | and pharmaceutically acceptable acid addition salts thereof.

Representative Chemical Abstracts Service (CAS) Index-like names for compounds of the present invention were derived using the ACD/LABS SOFTWARE™ Index Name Pro Version 4.5 nomenclature software program provided Advanced Chemistry Development, Inc., Toronto, Ontario, Canada.

In another view, exemplified compounds of the present invention include those compounds shown in Table 2 (the atom numbering indicates the ring position at which the $R^4$ substituent(s) is(are) attached) of the general formula:

TABLE 2

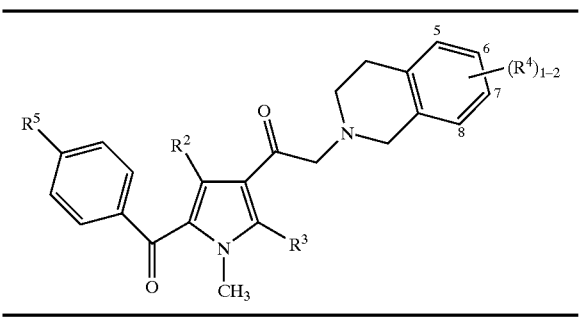

wherein $R^2$, $R^3$, $R^4$ and $R^5$ are selected from

| Cpd | $R^2$, $R^3$ | $R^4$ | $R^5$ |
|---|---|---|---|
| 1 | H, H | 6-OCH$_3$, 7-OCH$_3$ | F; |
| 2 | H, H | 6-H, 7-H | F; |
| 3 | CH$_3$, CH$_3$ | 6-OCH$_3$, 7-OCH$_3$ | Cl; |

-continued

| Cpd | $R^2$, $R^3$ | $R^4$ | $R^5$ |
|---|---|---|---|
| 4 | H, H | 6-OCH$_3$, 7-OCH$_3$ | CH$_3$S; |
| 5 | H, H | 6-OCH$_3$, 7-OCH$_3$ | H; |
| 6 | H, H | 6-H, 7-H | H; |
| 7 | H, H | 6-OCH$_3$, 7-OCH$_3$ | CH$_3$SO$_2$; or, |
| 8 | H, H | 6-OCH$_3$, 7-OCH$_3$ | CH$_3$SO; | and pharmaceutically acceptable acid addition salts thereof.

The compounds of the present invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharic or trifluoroacetic.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The terms used in describing the invention are commonly used and known to those skilled in the art. However, the terms that could have other meanings are hereinafter defined. These definitions apply to the terms as they are used throughout this specification, unless otherwise limited in specific instances, either individually or as part of a larger group.

An "independently" selected substituent refers to a group of substituents, wherein the substituents may be different. Therefore, designated numbers of carbon atoms (e.g., $C_1$–$C_6$) shall refer independently to the number of carbon atoms in an alkyl chain or to the alkyl portion of a larger substituent in which alkyl appears as its prefix root.

The term "alkyl" refers to straight and branched-chain alkyl radical groups and the term "alkylene" refers to a corresponding straight and branched-chain alkyl linking group. The term "alkoxyl" refers to O-alkyl groups where alkyl is as defined supra.

The term aryl refers to a single aromatic ring of six carbon members or a bicyclic aromatic ring of ten carbon members. Examples of such aryl rings include phenyl and naphthyl.

The term heteroaryl refers to an aromatic ring of five or six members wherein the ring has at least one heteroatom member. Suitable heteroatoms include nitrogen, oxygen or sulfur. In the case of five membered rings, the heteroaryl ring contains one member of nitrogen, oxygen or sulfur and, in addition, may contain up to two additional nitrogens. In the case of six-membered rings, the heteroaryl ring may contain from one to three nitrogen atoms. For the case wherein the six member ring has three nitrogens, at most two nitrogen atoms are adjacent. Examples of such heteroaryl rings include furyl, thienyl, pyrrolyl, pyrrolinyl, oxazolyl, thiazolyl, imidazolyl, imidazolinyl, pyrazolyl, pyrazolinyl, isoxazolyl, isothiazolyl, 1,2,3-oxadiazolyl, 1,2,3-triazolyl, 1,3,4-thiadiazolyl, pyranyl, pyridinyl, pyridazinyl, pyrimidinyl, pyrazinyl and 1,3,5triazinyl.

The terms "aryl($C_{1-4}$)alkyl" or "hydroxy($C_{1-4}$)alkyl" refer to an alkylene group substituted at the terminal carbon with an aryl or hydroxy group, respectively. Similarly, the terms "$C_{1-4}$alkylthio," "$C_{1-4}$alkylsulfinyl" and "$C_{1-4}$alkylsulfonyl" refer to a thio, sulfinyl or sulfonyl linking group substituted with a terminal alkyl group.

Whenever the term "alkyl" or "aryl" or either of their prefix roots appear in a name of a substituent (e.g., aryl($C_{1-4}$)alkyl) it shall be interpreted as including those limitations given above for "alkyl" and "aryl." Designated numbers of carbon atoms (e.g., $C_{1-6}$) shall refer independently to the number of carbon atoms in an alkyl or cycloalkyl moiety or to the alkyl portion of a larger substituent in which alkyl appears as its prefix root.

The term "hydroxy" refers to the group —OH.

The term "halogen" or "halo" shall include iodine, bromine, chlorine and fluorine.

Exemplary substituents include one or more alkyl groups as described above or one or more groups described above as substituted alkyl.

The novel compounds of Formula (I) and Formula (II) are useful as agents for the treatment of central nervous system disorders. Examples of central nervous system disorders include, but are not limited to, epilepsy and neuropathic pain. The utility of the instant compounds can be determined according to the procedures described herein.

An embodiment of the invention is a pharmaceutical composition comprising one or more compounds of this invention in association with a pharmaceutically acceptable carrier. Another embodiment is a pharmaceutical composition made by mixing any of the compounds described above and a pharmaceutically acceptable carrier. A further embodiment is a process for making a pharmaceutical composition comprising mixing any of the compounds described above and a pharmaceutically acceptable carrier.

To prepare the pharmaceutical compositions of this invention, one or more compounds of Formula (I) or Formula (II) or salt thereof, as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The present invention includes a method for treating a central nervous system disorder using the isoindolyl and isoquinolinyl aroyl pyrrole compounds of the present invention.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The present invention therefore provides a method for the use of an active compound selected from Formula (I) and Formula (II) to treat a central nervous system disorder in a subject in need thereof which comprises administering any of the compounds as defined herein in a therapeutically effective dose to mediate the disorder. In particular, the present invention also includes a method for the use of an active compound selected from Formula (I) and Formula (II) to treat epilepsy or the symptoms of epilepsy in a subject in need thereof which comprises administering any of the compounds as defined herein in a therapeutically effective dose to inhibit epilepsy.

A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

A therapeutically effective dose for use of the instant compounds or a pharmaceutical composition thereof to treat a central nervous system disorder comprises a dose range of from about 0.01 mg to about 12,000 mg, in particular from about 0.1 mg to about 4000 mg or, more particularly from about 1 mg to about 2000 mg of active ingredient per day for an average (70 kg) human.

For treating epilepsy, a therapeutically effective dose for use of the instant compounds or a pharmaceutical composition thereof comprises a dose range of from about 0.01 mg to about 12,000 mg, in particular from about 0.1 mg to about 4000 mg or, more particularly from about 1 mg to about 2000 mg of active ingredient per day for an average (70 kg) human.

In general, a compound having Formula (I) and Formula (II) or a pharmaceutical composition thereof may be used in treating epilepsy in a manner similar to that used for phenytoin. Medical aspects of the treatment of epilepsy are described in L. S. Goodman, et. al., in "The Pharmacological Basis of Therapeutics", 5th Ed. pages 201 to 226, Macmillan (1975).

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. More preferably, a unit dose would contain from about 10 mg to about 500 mg of the active ingredient. Advantageously, compounds of the present invention may be administered in a single daily dose or the total daily dosage may be administered in divided doses of two, three or four times daily.

It is apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Compounds of this invention may be administered in any of the foregoing compositions and dosage regimens or by means of those compositions and dosage regimens established in the art whenever use of the compounds of the invention to treat a central nervous system disorder is required for a subject in need thereof.

The terms used in describing the invention are commonly used and known to those skilled in the art. As used herein, the following abbreviations have the indicated meanings:

| | |
|---|---|
| $AlCl_3$ | Aluminum chloride |
| DCE | 1,2-dichloroethane |
| $Et_2O$ | Diethyl ether |
| EtOH | Ethanol |
| H | Hour |
| $K_2CO_3$ | Potassium carbonate |
| MeOH | Methanol |
| $NaBH_4$ | Sodium borohydride |
| $NaBH(OAc)_3$ | Sodium triacetoxyborohydride |
| NaOt-Bu | Sodium tert-butoxide |
| Min | Minute |
| 2-PrOH | 2-Propanol |
| Rt | Room temperature |
| $TiCl_4$ | Titanium (IV) tetrachloride |

General Synthetic Methods

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

Instant compounds useful as agents for the treatment of central nervous system disorders may be placed into two categories, those having an aromatic ring at the 2-carbonyl position and those having an aromatic ring at the 4-carbonyl position. Both categories of compounds may be prepared by variations of what is fundamentally the same reaction scheme.

Scheme A exemplifies the preparation of compounds having the optionally substituted aryl or heteroaryl ring at the 2-position. Referring to Scheme A, in the first step a simple pyrrole Compound A1 is acylated with an appropriately substituted benzoyl chloride Compound A2 to produce a benzoyl pyrrole Compound A3.

One method of acylation involves simply heating the aroyl chloride Compound A2 and the pyrrole Compound A1 in an aprotic solvent followed by removing excess aroyl chloride by reaction with a dibasic amine and extraction with HCl. In the case where the substituents on pyrrole Compound A1 affect the yield, a Vilsmeier type acylation (J. White and G. McGillivrey, *J. Org. Chem.,* 1977, 42, 42–48) may be expeditiously employed.

The temperature of the acylation will vary depending upon the desired rate of reaction and the substituents on pyrrole Compound A1. Preferably the acylation is carried out at a temperature of from 50° C. to 250° C. A suitable dibasic amine is dimethyl-3-aminopropyl amine.

Subsequently, the benzoyl pyrrole Compound A3 is acylated at the 4-position in a Friedel-Crafts reaction with the halogenated alkanoyl acid chloride Compound A4 to produce a 2-benzoyl-4-halogenated alkanoyl pyrrole Compound A5. The Friedel-Crafts reaction is carried out by refluxing the halogenated carboxylic acid chloride Compound A4 (in which X is Cl, Br or I), Compound A3 in a solvent and a Friedel-Crafts reagent followed by treatment with HCl and evaporation of the solvent. Suitable Friedel-Crafts reagents include aluminum chloride, zinc chloride, $BF_3$ or $TiCl_4$. Suitable solvents include methylene chloride, 1,2-dichloroethane, carbon tetrachloride or chloroform. The temperature of reflux might vary between 30 and 150° C.

To produce Compound A7, the 2-benzoyl-4-halogenated alkanoyl pyrrole Compound A5 is aminated with an isoindolyl or isoquinolinyl Compound A6 to produce the substituted aroyl pyrrole Compound A7. The amination may be carried out by heating the reactants Compound A5 and Compound A6 neat or in a solvent to a temperature of from 40 to 120° C. and preferably from 50 to 90° C. Suitable solvents, where employed, include ethanol, i-propanol or toluene.

SCHEME A

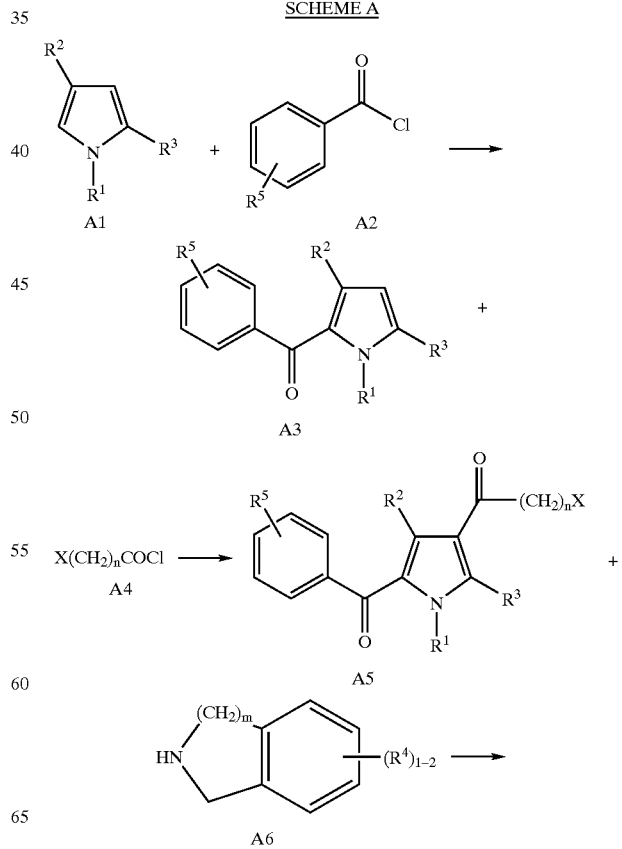

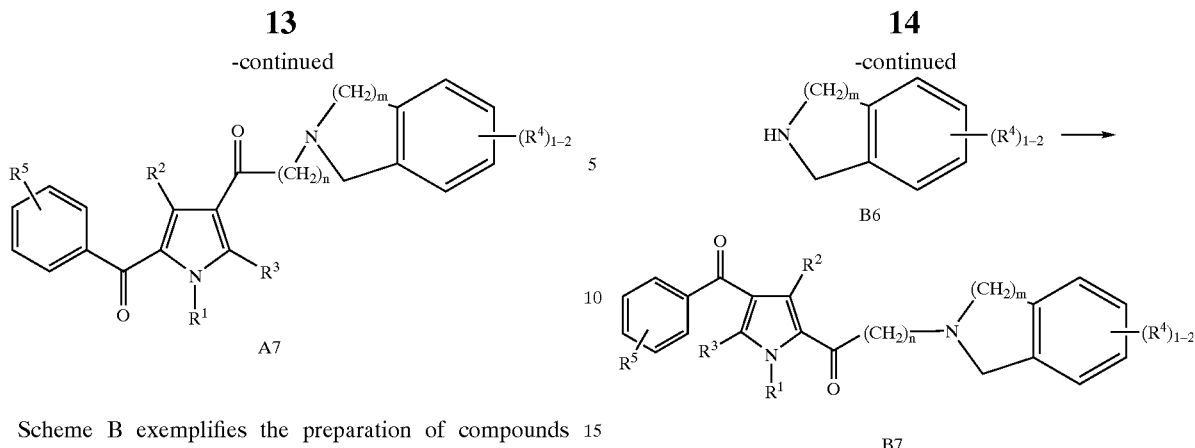

Scheme B exemplifies the preparation of compounds having an aromatic ring at the 4-position. Except for the specifics of the reactants, each step of Scheme B is analogous to the corresponding step of Scheme A with the reactions and description thereof being identical. Referring to Scheme B, in the first step a simple pyrrole Compound B1 is acylated with an appropriately substituted halogenated alkanoyl acid chloride Compound B2 to produce a 2-halogenated alkanoyl pyrrole Compound B3. Subsequently, the alkanoyl pyrrole Compound B3 is acylated at the 4-position in a Friedel-Crafts reaction with a benzoyl chloride Compound B4 to produce a 2-halogenated alkanoyl-4-benzoyl pyrrole Compound B5. In the third reaction, the halogenated alkanoyl benzoyl pyrrole Compound B5 is aminated with an isoindolyl or isoquinolinyl Compound B6 to produce the substituted aroyl pyrrole Compound B7.

SCHEME B

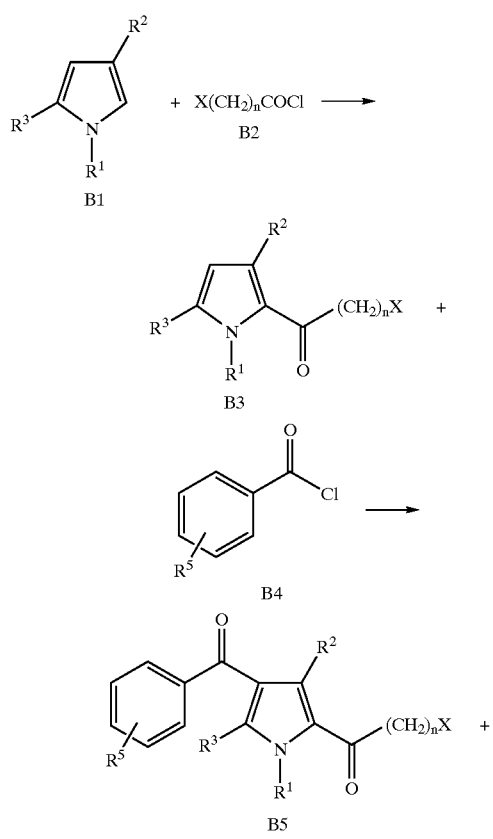

The compounds herein readily form pharmaceutically acceptable acid addition salts. Such salts include hydrochlorides, sulfates, phosphates, methane sulfonates, fumarates, maleates, citrates, lactates, and the like. Those skilled in the art will readily recognize suitable methods for manufacture and use of the acid addition salts.

Specific Synthetic Methods

Specific compounds which are representative of this invention may be prepared as per the following examples offered by way of illustration and not by way of limitation. Also, examples specifically used to prepare intermediates for the further synthesis of compounds of the invention are designated by "Procedure." No attempt has been made to optimize the yields obtained in any of the reactions. One skilled in the art would know how to increase such yields through routine variations in reaction times, temperatures, solvents and/or reagents.

Procedure 1

2-Chloro-1-[1-methyl-5-[4-(methylsulfinyl) benzoyl]-1H-pyrrol-3-yl]-ethanone

A mixture of 2.5 g (0.008 mole) of 2-chloro-1-[1-methyl-5-(4-(methylthio)benzoyl]-1H-pyrrol-3-yl]-ethanone, 1.2 g of sodium perborate tetrahydrate and 50 mL of HOAc was stirred for 3 h. The solvent was evaporated in vacuo and the residue partitioned between $CH_2Cl_2$ and $NaHCO_3$. The organics were separated off and washed again with $NaHCO_3$, water, brine and dried ($Na_2SO_4$). The solvent was evaporated in vacuo. The residue was passed through a Biotage flash 40 L column (silica gel 9:1 $CH_2Cl_2$: MeOH) to give 2.2 g (85%) of 2-chloro-1-[1-methyl-5-(4-(methylsulfinyl)benzoyl]-1H-pyrrol-3-yl]-ethanone. CIMS m/z=324 (MH$^+$). HNMR (CDCl$_3$) $\delta$8.0 (d, 2H); 7.75 (d, 2H); 7.6 (s, 1H); 7.15 (s, 1H); 4.4 (s, 2H); 4.1 (2, 3H); 2.8 (s, 3H).

Procedure 2

2-Chloro-1-[1-methyl-5-[4-(methylsulfonyl) benzoyl]-1H-pyrrol-3-yl]-ethanone

A mixture of 2.5 g (0.0074 mole) of 2-chloro-1-[1-methyl-5-(4-(methylsulfinyl)benzoyl]-1H-pyrrol-3-yl]-ethanone, 20 mL of HOAc, and 1.7 mL of 30% $H_2O_2$ was stirred for 6 days. The solid was filtered off to give 0.75 g (30%) of 2-chloro-1-[1-methyl-5-(4-(methylsulfonyl) benzoyl]-1H-pyrrol-3-yl]-ethanone. HNMR (CDCl$_3$) $\delta$8.1 (s, 2H); 8.0 (s, 2H); 7.7 (ar, 1H); 7.1 (ar, 1H); 4.4 (s, 2H); 4.1 (s, 3H); 3.1 (s, 3H).

EXAMPLE 1

2-(3,4-dihydro-6,7-dimethoxy-2(1H)-isoquinolinyl)-1-[1-methyl-5-[4-(methylthio)benzoyl]-1H-pyrrol-3-yl]-ethanone (Compound 4)

A mixture of 1.5 g (0.0049 mole) of 2-chloro-1-[1-methyl-5-(4-methylthiobenzoyl)-1H-pyrrol-3-yl]-ethanone, 1.7 g (0.0074 mole) of 6,7-dimethoxy-1,2,3,4-tetrahydroisoquinoline hydrochloride, 1.9 mL (0.01 mole) diisopropylethylamine and 40 mL of 2-PrOH was refluxed for 3 h and then the solvent was evaporated in vacuo. The residue was partitioned between $Et_2O$-THF and $NaHCO_3$, the organics were separated off, washed with water, brine and dried ($Na_2SO_4$). The solvent was evaporated in vacuo. The residue was passed through a Biotage Flash 40 L column (silica gel, 9:1; $CH_2Cl_2$:MEOH) and the product was converted to the hydrochloride salt with ethereal HCl in EtOH to give 0.58 g (25%) of Compound 4 mp. 231–233° C. CIMS m/z=465 ($MH^+$). HNMR (DMSO-$d_6$) δ8.2 (s, 1H); 7.8 (d, 2H); 7.4 (d, 2H); 7.2 (s, 1H); 6.8 (d, 2H); 4.8 (s, 2H); 4.5 (m, 1H); 4.3 (m, 1H); 4.0 (s, 3H); 3.7 (d, 6H); 3.65 (m, 1H); 3.4 (m, 1H); 3.05 (m, 2H); 2.6 (s, 3H).

EXAMPLE 2

Using the procedure for Example 1, the following compounds were prepared.

| Cpd | MS m/z ($MH^+$) |
|---|---|
| 1 | 437 |
| 2 | 377 |
| 3 | 481 |
| 5 | 419 |
| 6 | 359 |
| 7 | 497 |
| 8 | 481 |

Biological Examples

The compounds of the present invention are useful as agents for the treatment of central nervous system disorders. The following biological examples demonstrate the use of the instant compounds in a method for the treatment of central nervous system disorders including, but not limited to, use as anticonvulsants, antiepileptics, neuroprotective agents, muscle relaxants and as agents for the treatment of neuropathic pain.

Procedure for Testing in Mouse Anticonvulsant Model

The compounds of Formula (I) and Formula (II) are useful as anticonvulsant agents. The anticonvulsant activity of the subject compounds is determined using a standard "maximal electroshock test" (MES). In this test, activity is indicated by a block of the toxic extensor seizure, as described by Swinyard, et al., in *J. Pharmacol. Exptl. Therap.*, 106, 319 (1952). A more recent description of current anticonvulsant drug screening is given in Swinyard, et al., in *Epilepsia*, 19, 409 (1978).

Procedure for Testing in a Neuropathic Pain Model

The compounds of the present invention are useful in the treatment of neuropathic pain. The use of the compounds in treating neuropathic pain is as determined using an animal model. This model was developed and first described by S. H. Chung and J. M. Chung, An Experimental Model for Peripheral Neuropathy Produced by Segmental Spinal Nerve Ligation in the Rat, *Pain*, 1992, 50, 355–363 (referred to hereinafter as the "Chung Model").

Male Sprague-Dawley rats, weighing approximately 200 g each are anesthetized with isoflurane. The spinal nerve at the level of $L_5$ is exposed through an incision just left of the dorsal midline and tightly ligated with 6–0 silk. At various times after surgery, animals are tested for mechanical allodynia with von Frey hairs (monofilaments which are calibrated to bend under a certain amount of pressure, ranging from 0.41 to 15.1 g). In order to calculate a paw withdrawal threshold (PWT), tactile allodynia is measured by recording the pressure at which the affected paw is withdrawn from graded stimuli according to the procedure of S. R. Chaplan, J. W. Pogrel, T. L. Yaksh, Role of Voltage-Dependent Calcium Channel Subtypes in Experimental Tactile Allodynia, *J. Pharmacol. Exp. Ther.* 1994, 269, 1117–1123. Normal rats can withstand at least 15 g of pressure without responding. Operated rats, however, can respond to as little as 0.25 g of pressure. The surgery is deemed successful if the animal responded with a PWT of less than 4 g of pressure applied to the affected paw.

The sham operation consists of a similar surgery; the spinal nerve is visualized without being ligated. These animals are also tested for mechanical allodynia and should show no response to greater than 15 g of force applied to the ipsilateral paw. The results of the assay are expressed as percent of the maximum possible effect (% MPE), calculated as the PWT at the time of testing minus the baseline PWT divided by the maximum PWT (15 g) minus the baseline PWT times 100.

The compounds having Formula (I) and Formula (II) are tested for activity against neuropathic pain by being dissolved or suspended in either water or hydroxypropyl methylcellulose, respectively. Postoperative animals between 14 to 42 days are fasted overnight prior to dosing. Animals are orally dosed and dosage volumes are calculated on a 4 mL/kg basis. The screening dose employed is 30 mg/kg.

What is claimed is:

1. A compound of Formula (I) and Formula (II):

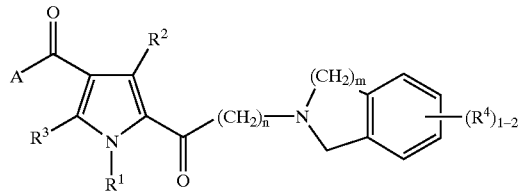

Formula (I)

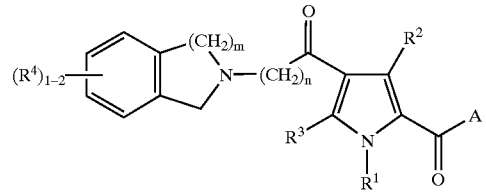

Formula (II)

wherein

A is selected from the group consisting of aryl and heteroaryl optionally substituted with one to two substituents independently selected from the group consisting of $C_{1-4}$alkyl, $C_{1-4}$alkoxy, aryl, aryl($C_{1-4}$)alkyl, amino (optionally substituted with one or two substituents independently selected from $C_{1-4}$alkyl), amino($C_{1-4}$)alkyl (wherein amino is optionally substituted with one or two substituents independently selected from $C_{1-4}$alkyl), $C_{1-4}$alkylthio, $C_{1-4}$alkylsulfinyl, $C_{1-4}$alkylsulfonyl, halogen, tri(halo)$C_{1-4}$alkyl, tri(halo)$C_{1-4}$alkoxy, hydroxy, hydroxy$C_{1-4}$alkyl, cyano and nitro;

R¹, R² and R³ are independently selected from the group consisting of hydrogen and C$_{1-4}$alkyl;

R⁴ is independently selected from the group consisting of hydrogen, C$_{1-4}$alkyl, C$_{1-4}$alkoxy, aryl, aryl(C$_{1-4}$)alkyl, amino (optionally substituted with one or two substituents independently selected from C$_{1-4}$alkyl), amino(C$_{1-4}$)alkyl (wherein amino is optionally substituted with one or two substituents independently selected from C$_{1-4}$alkyl), halogen, tri(halo)C$_{1-4}$alkyl, tri(halo)C$_{1-4}$alkoxy, hydroxy, hydroxyC$_{1-4}$alkyl, cyano and nitro;

n is an integer from 1 to 5; and, m is an integer from 1 to 2;

and pharmaceutically acceptable acid addition salts thereof; with the proviso that a compound selected from Formula (I) cannot be 2-(3,4-dihydro-6,7-dimethoxy-2(1H)-isoquinolinyl)-1-[5-(4-methoxybenzoyl)-1-methyl-1H-pyrrol-3-yl]-ethanone.

2. The compound of claim 1 wherein A is phenyl optionally substituted with one to two substituents independently selected from the group consisting of C$_{1-4}$alkyl, C$_{1-4}$alkoxy, phenyl, phenyl(C$_{1-4}$)alkyl, amino (optionally substituted with one or two substituents independently selected from C$_4$alkyl), amino(C$_{1-4}$)alkyl (wherein amino is optionally substituted with one or two substituents independently selected from C$_{1-4}$alkyl), C$_{1-4}$alkylthio, C$_{1-4}$alkylsulfinyl, C$_{1-4}$alkylsulfonyl, halogen, trifluoroC$_{1-4}$alkyl, trifluoro C$_{1-4}$alkoxy, hydroxy, hydroxyC$_{1-4}$alkyl, cyano and nitro.

3. The compound of claim 1 wherein A is phenyl optionally substituted with one to two substituents independently selected from the group consisting of methyl, ethyl, n-propyl, n-butyl, i-butyl, t-butyl, methoxy, ethoxy, propoxy, phenyl, benzyl, phenethyl, phenylpropyl, amino, N—(C$_{1-3}$alkyl)amino, N,N-di(C$_{1-3}$alkyl)amino, amino(C$_{1-3}$)alkyl, N—(C$_{1-3}$alkyl)amino(C$_{1-3}$)alkyl, N,N-di(C$_{1-3}$alkyl)amino(C$_{1-3}$)alkyl, methylthio, ethylthio, n-propylthio, n-butylthio, i-butylthio, methylsulfinyl, ethylsulfinyl, n-propylsulfinyl, n-butylsulfinyl, i-butylsulfinyl, methylsulfonyl, ethylsulfonyl, n-propylsulfonyl, n-butylsulfonyl, i-butylsulfonyl, chlorine, fluorine, trifluoromethyl, trifluoromethoxy, hydroxy, hydroxymethyl, hydroxyethyl and hydroxypropyl.

4. The compound of claim 1 wherein A is phenyl optionally substituted with one to two substituents independently selected from the group consisting of methoxy, methylthio, methylsulfinyl, methylsulfonyl, chlorine and fluorine.

5. The compound of claim 1 wherein R¹, R² and R³ are independently selected from the group consisting of hydrogen, methyl, ethyl and propyl.

6. The compound of claim 1 wherein R¹, R² and R³ are independently selected from the group consisting of hydrogen and methyl.

7. The compound of claim 1 wherein R⁴ is independently selected from the group consisting of hydrogen, C$_{1-4}$alkyl, C$_{1-4}$alkoxy, phenyl, phenyl(C$_{1-4}$)alkyl, amino (optionally substituted with one or two substituents independently selected from C$_{1-4}$alkyl), amino(C$_{1-4}$)alkyl (wherein amino is optionally substituted with one or two substituents independently selected from C$_{1-4}$alkyl), halogen, trifluoro C$_{1-4}$alkyl, trifluoroC$_{1-4}$alkoxy, hydroxy, hydroxyC$_{1-4}$alkyl, cyano and nitro.

8. The compound of claim 1 wherein R⁴ is independently selected from the group consisting of hydrogen, methyl, ethyl, n-propyl, n-butyl, i-butyl, t-butyl, methoxy, ethoxy, propoxy, phenyl, benzyl, phenethyl, phenylpropyl, amino, N—(C$_{1-3}$alkyl)amino, N,N-di(C$_{1-3}$alkyl)amino, amino(C$_{1-3}$)alkyl, N—(C$_{1-3}$alkyl)amino(C$_{1-3}$)alkyl, N,N-di(C$_{1-3}$alkyl)amino(C$_{1-3}$)alkyl, chlorine, fluorine, trifluoromethyl, trifluoromethoxy, hydroxy, hydroxymethyl, hydroxyethyl and hydroxypropyl.

9. The compound of claim 1 wherein R⁴ is independently selected from the group consisting of hydrogen and methoxy.

10. The compound of claim 1 wherein n is an integer from 1 to 2.

11. The compound of claim 1 selected from the group consisting of 2-(3,4-dihydro-6,7-dimethoxy-2(1H)-isoquinolinyl)-1-[5-(4-fluorobenzoyl)1-methyl-1H-pyrrol-3-yl]-ethanone;

2-(3,4-dihydro-2(1H)-isoquinolinyl)-1-[5-(4-fluorobenzoyl)-1-methyl-1H-pyrrol-3-yl]-ethanone;

1-[5-(4-chlorobenzoyl)-1,2,4-trimethyl-1H-pyrrol-3-yl]-2-(3,4-dihydro-6,7-dimethoxy-2(1H)-isoquinolinyl)-ethanone;

2-(3,4-dihydro-6,7-dimethoxy-2(1H)-isoquinolinyl)-1-[1-methyl-5-[4-(methylthio)benzoyl]-1H-pyrrol-3-yl]-ethanone;

1-(5-benzoyl-1-methyl-1H-pyrrol-3-yl)-2-(3,4-dihydro-6,7-dimethoxy-2(1H)-isoquinolinyl)-ethanone;

1-(5-benzoyl-1-methyl-1H-pyrrol-3-yl)-2-(3,4-dihydro-2(1H)-isoquinolinyl)-ethanone;

2-(3,4-dihydro-6,7-dimethoxy-2(1H)-isoquinolinyl)1-[1-methyl-5-[4-(methylsulfonyl)benzoyl]-1H-pyrrol-3-yl]-ethanone; and, 2-(3,4-dihydro-6,7-dimethoxy-2(1H)-isoquinolinyl)-1-[1-methyl-5-[4-(methylsulfinyl)benzoyl]-1H-pyrrol-3-yl]-ethanone;

and pharmaceutically acceptable acid addition salts thereof.

12. The compound of claim 1 of the formula:

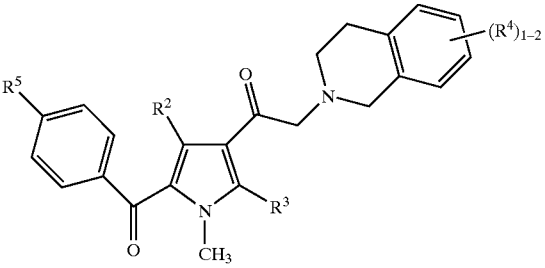

wherein R², R³, R⁴ and R⁵ are dependently selected from the group consisting of

| R², R³ | R⁴ | R⁵ |
|---|---|---|
| H, H | 6-OCH₃, 7-OCH₃ | F; |
| H, H | 6-H, 7-H | F; |
| CH₃, CH₃ | 6-OCH₃, 7-OCH₃ | Cl; |
| H, H | 6-OCH₃, 7-OCH₃ | CH$_{3l S;}$ |
| H, H | 6-OCH₃, 7-OCH₃ | H; |
| H, H | 6-H, 7-H | H; |
| H, H | 6-OCH₃, 7-OCH₃ | CH₃SO₂; and, |
| H, H | 6-OCH₃, 7-OCH₃ | CH₃SO; | and pharmaceutically acceptable acid addition salts thereof.

13. The compound of claim 1 which is an effective agent for the treatment of central nervous system disorders.

14. The compound of claim 1 wherein the agent is selected from the group consisting of anticonvulsant agents, antiepileptic agents, neuroprotective agents, muscle relaxant agents and agents for the treatment of neuropathic pain.

15. A pharmaceutical composition comprising a compound of claim 1 in association with a pharmaceutically acceptable carrier.

16. A pharmaceutical composition made by mixing a compound of claim 1 and a pharmaceutically acceptable carrier.

17. A method for making a pharmaceutical composition comprising mixing a compound of claim 1 and a pharmaceutically acceptable carrier.

18. A method for treating a central nervous system disorder in a subject in need thereof comprising administering to the subject a compound of claim 1 in a therapeutically effective dose to mediate the central nervous system disorder.

19. The method of claim 18 wherein the therapeutically effective dose is from about 0.01 mg/day to about 12,000 mg/day.

20. The method of claim 18 wherein the central nervous system disorder is selected from the group consisting of epilepsy and neuropathic pain.

21. The method of claim 18 wherein the compound of claim 1 is administered as an anticonvulsant agent, antiepileptic agent, neuroprotective agent, muscle relaxant agent and agent for the treatment of neuropathic pain.

22. A method for treating epilepsy or the symptoms of epilepsy in a subject in need thereof comprising administering to the subject a compound of claim 1 in a therapeutically effective dose to mediate epilepsy or the symptoms of epilepsy.

23. The method of claim 22 wherein the therapeutically effective dose is from about 0.01 mg/day to about 12,000 mg/day.

* * * * *